United States Patent
Kroll et al.

(10) Patent No.: US 7,403,823 B1
(45) Date of Patent: Jul. 22, 2008

(54) SUPER PLASTIC DESIGN FOR CHF PACEMAKER LEAD

(75) Inventors: Mark W. Kroll, Orono, MN (US); John R. Helland, Saugus, CA (US); Yougandh Chitre, Valencia, CA (US); Michael Yang, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 258 days.

(21) Appl. No.: 11/205,865

(22) Filed: Aug. 16, 2005

(51) Int. Cl.
*A61N 1/05* (2006.01)
(52) U.S. Cl. ................................ 607/119
(58) Field of Classification Search ........... 607/116, 607/119, 122, 123
See application file for complete search history.

(56) References Cited

U.S. PATENT DOCUMENTS

| | | | | |
|---|---|---|---|---|
| 4,154,247 A | * | 5/1979 | O'Neill | 607/125 |
| 4,411,962 A | | 10/1983 | Johnson | 428/615 |
| 4,856,529 A | * | 8/1989 | Segal | 600/454 |
| 5,016,805 A | | 5/1991 | Cadwell | 228/118 |
| 5,217,548 A | | 6/1993 | Kuboki et al. | 148/671 |
| 5,360,441 A | * | 11/1994 | Otten | 607/122 |
| 5,415,633 A | * | 5/1995 | Lazarus et al. | 604/95.05 |
| 5,441,483 A | * | 8/1995 | Avitall | 604/95.05 |
| 5,722,425 A | * | 3/1998 | Bostrom | 600/585 |
| 6,116,070 A | | 9/2000 | Oshida et al. | 72/60 |
| 6,295,475 B1 | | 9/2001 | Morgan | 607/122 |
| 6,325,797 B1 | * | 12/2001 | Stewart et al. | 606/41 |
| 6,451,034 B1 | | 9/2002 | Gifford, III et al. | 606/153 |
| 6,490,489 B2 | | 12/2002 | Bornzin et al. | 607/122 |
| 6,512,957 B1 | * | 1/2003 | Witte | 607/116 |
| 6,607,693 B1 | | 8/2003 | Saito et al. | 420/417 |
| 6,623,480 B1 | * | 9/2003 | Kuo et al. | 606/41 |
| 6,650,945 B2 | | 11/2003 | Helland et al. | 607/122 |
| 2001/0007070 A1 | * | 7/2001 | Stewart et al. | 606/41 |
| 2002/0103524 A1 | | 8/2002 | Bornzin et al. | 607/122 |

FOREIGN PATENT DOCUMENTS

EP 1352978 A1 10/2003

OTHER PUBLICATIONS

Saito, Takashi, et al., "Multifunctional Alloys Obtained via a Dislocation-Free Plastic Deformation Mechanism", *Science Magazine*, Apr. 2003: vol. 300, pp. 464-467.

* cited by examiner

*Primary Examiner*—Carl H. Layno
*Assistant Examiner*—Jon-Eric C. Morales

(57) ABSTRACT

An implantable lead assembly for a body implantable medical system adapted to transmit electrical signals between a proximal end portion of the lead assembly and a distal end portion of the lead assembly to thereby stimulate selected body tissue includes an elongated insulative sheath of flexible resilient material having at least one longitudinally extending lumen, an electrical conductor received within the lumen of the insulative sheath and extending between a proximal end and a distal end, and at least one elongated super plastic element slidably received within the lumen of the insulative sheath, the super plastic element being bendable to configure the lead assembly to negotiate tortuous turns in the vasculature of the body. An electrical connector is coupled to the proximal end of the conductor for releasable attachment to a stimulating pulse generator and an electrode is coupled to the distal end of the conductor.

19 Claims, 4 Drawing Sheets

SUPER PLASTIC DESIGN FOR CHF PACEMAKER LEAD

FIELD OF THE INVENTION

The present invention relates generally to lead assemblies for connecting implantable medical devices with selected body tissue to be stimulated by such devices and, more particularly, to such lead assemblies which are capable of negotiating tortuous turns in the vasculature of the body.

BACKGROUND OF THE INVENTION

Implantable cardiac stimulation devices are well known in the art. Such devices may include, for example, implantable cardiac pacemakers and defibrillators. The devices are generally implanted in a pectoral region of the chest beneath the skin of a patient within what is known as a subcutaneous pocket. The implantable devices generally function in association with one or more electrode carrying leads which are implanted within the heart. The electrodes are usually positioned within the right side of the heart, either within the right ventricle or right atrium, or both, for making electrical contact with their respective heart chamber. Conductors within the leads couple the electrodes to the device to enable the device to sense cardiac electrical activity and deliver the desired therapy.

Traditionally, therapy delivery had been limited to the venous, or right side of the heart. The reason for this is that implanted electrodes can cause blood clot formation in some patients. If a blood clot were released arterially from the heart left side, as for example the left ventricle, it could pass directly to the brain potentially resulting in a paralyzing or fatal stroke. However, a blood clot released from the right heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy to the left heart. These lead structures and methods avoid direct electrode placement within the left atrium and left ventricle of the heart by lead implantation within the coronary sinus region of the heart. As used herein, the phrase "coronary sinus region" refers to the venous vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

It has been demonstrated that electrodes placed in the coronary sinus region of the heart may be used for left atrial pacing, left ventricular pacing, and cardioversion and defibrillation. These advancements enable implantable cardiac stimulation devices to address the needs of a patient population with left ventricular dysfunction and/or congestive heart failure which would benefit from left heart side pacing, either alone or in conjunction with right heart side pacing (bi-chamber pacing), and/or defibrillation. Many present CHF devices require both a lead in the left ventricle (LV) and a separate lead in the right ventricle (RV), the RV lead intended for pacing the right ventricular apex or tip of the right ventricle while the LV lead is for pacing the left ventricle to obtain better synchronization together which results in improved hemodynamics. The significance of a single lead for positioning only in the left ventricle is that it is easier and less time consuming to install only one lead rather than two and, additionally two leads can "saw" against each other where they cross in the RA (right atrium), potentially resulting in damage to their insulation.

By pacing simultaneously from the distal, apical electrode to the more proximal, basal electrode ring in the LV, a more efficient contraction is obtained, with improved cardiac output, and patients are found to have more energy. In this regard, it should be noted that the "simultaneous" stimulation is often better achieved when there is a time separation of up to 50 ms between the two sites.

Cardiac leads intended for use in providing both cardiac pacing and defibrillation in the left heart via the coronary sinus region have previously been difficult to position due to the tortuous venous routes of the human anatomy. Moreover, to provide both pacing and defibrillation of both the left atrium and the left ventricle from the coronary sinus region with multiple leads employing the appropriate types of electrodes is extremely difficult given the space constraints to accommodate multiple leads in the coronary sinus region. Hence, such known implants have been too cumbersome, difficult, and time consuming to perform and likely resulted in compromised performance or system malfunction.

Typical of known implantable cardiac leads for use in the coronary sinus region of the heart are U.S. Pat. Nos. 6,295,475 to Morgan entitled "Single-Pass Atrial Ventricular Lead with Multiple Atrial Ring Electrodes and a Selective Atrial Electrode Adapter for the Coronary Sinus Region", U.S. Pat. No. 6,490,489 to Bornzin et al. entitled "Implantable Cardiac Single Pass Coronary Sinus Lead for Providing Pacing and Defibrillation and Method of Manufacture", and 6,650,945 to Helland et al. entitled "Implantable Cardiac Coronary Sinus Lead Having a Defibrillation Electrode of Split Configuration and Method of Manufacture", as well as U.S. Publication No. US 2002/0103524 to Bornzin et al. entitled "Implantable Cardiac Single Pass Coronary Sinus Lead for Providing Pacing and Defibrillation and Method of Manufacture".

It was with knowledge of the foregoing state of the technology that the present invention has been conceived and is now reduced to practice.

SUMMARY

An implantable lead assembly for a body implantable medical system adapted to transmit electrical signals between a proximal end portion of the lead assembly and a distal end portion of the lead assembly to thereby stimulate selected body tissue includes an elongated insulative sheath of flexible resilient material having at least one longitudinally extending lumen, an electrical conductor received within the lumen of the insulative sheath and extending between a proximal end and a distal end, and at least one elongated super plastic element slidably received within the lumen of the insulative sheath, the super plastic element being bendable to configure the lead assembly to negotiate tortuous turns in the vasculature of the body. An electrical connector is coupled to the proximal end of the conductor for releasable attachment to a stimulating pulse generator and an electrode is coupled to the distal end of the conductor.

In operation, the lead would be inserted in an appropriate location and then a deflecting guide wire or introducer would be used to bend the lead to form it into a shape around corners and wedge against the walls of a vein, preventing its retraction. As another subtlety to this method, the super plastic titanium becomes more plastic with cold working. In other words, a physician could bend the lead back and forth until it became ductile to satisfy the physician's preferences. In this manner, the physician is able to "tune" the ductility of the lead to a better trade off of insertability and stability.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENTS

The following description is not to be taken in a limiting sense but is made merely for the purpose of describing the general principles of the illustrative embodiments. The scope of the invention should be ascertained with reference to the issued claims. In the description that follows, like numerals or reference designators will be used to refer to like parts or elements throughout.

Figure 1:
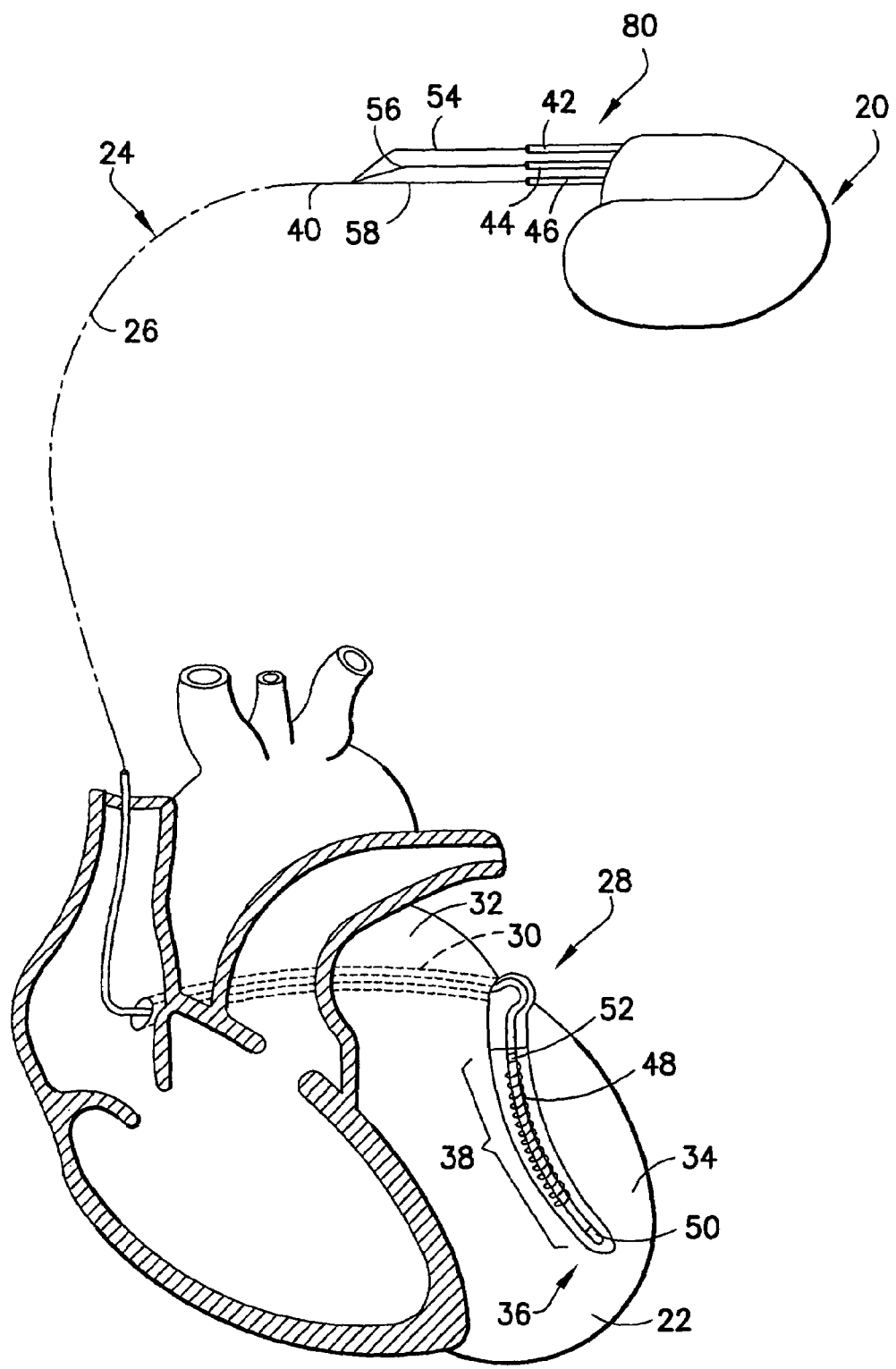
FIG. 1 is a diagrammatic perspective view illustrating an implantable cardiac stimulation device in electrical communication with a patient's heart by a coronary sinus region lead embodying the present invention.

As shown in FIG. 1, a stimulation device 20 is provided in electrical communication with a patient's heart 22 by way of a lead assembly 24 embodying the present invention intended for exemplary placement in the coronary sinus region 28. Lead assembly 24 provides both left ventricular pacing and defibrillation therapy. Designed for placement in the coronary sinus region of the heart, the lead assembly 24 extends through the coronary sinus ostium 30 and adjacent to the left atrium 32 and the left ventricle 34. As used herein, the phrase "coronary sinus region" refers to the venous vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

As will be noted in FIG. 1, the lead assembly 24 includes an elongated lead body 26 having a distal end 36 which includes an electrode assembly 38 and a proximal end 40 which extends to a plurality of terminals 42, 44, 46 at the proximal end of the lead body, each terminal being connected into the stimulation device 20 which includes a defibrillation electrode, preferably a conductive polymer electrode.

The electrode assembly 38 includes a defibrillation electrode 48 and first and second pacing electrodes 50, 52. The first pacing electrode 50 includes a distal tip or apical electrode at the distal end of the lead assembly which is spaced from the defibrillation electrode and positioned at, or adjacent to, the distal end of the lead body adjacent the apex of the left ventricle 34 of the heart 22. The second pacing electrode 52 includes a ring electrode which is spaced proximally from the defibrillation electrode 48 and adjacent the basal region of the left ventricle of the heart for stimulating the basal region. A plurality of conductors 54, 56, 58 serve to connect each electrode 48, 50, 52, via the respective terminals 42, 44, 46 to the stimulation device 20.

Figure 2:
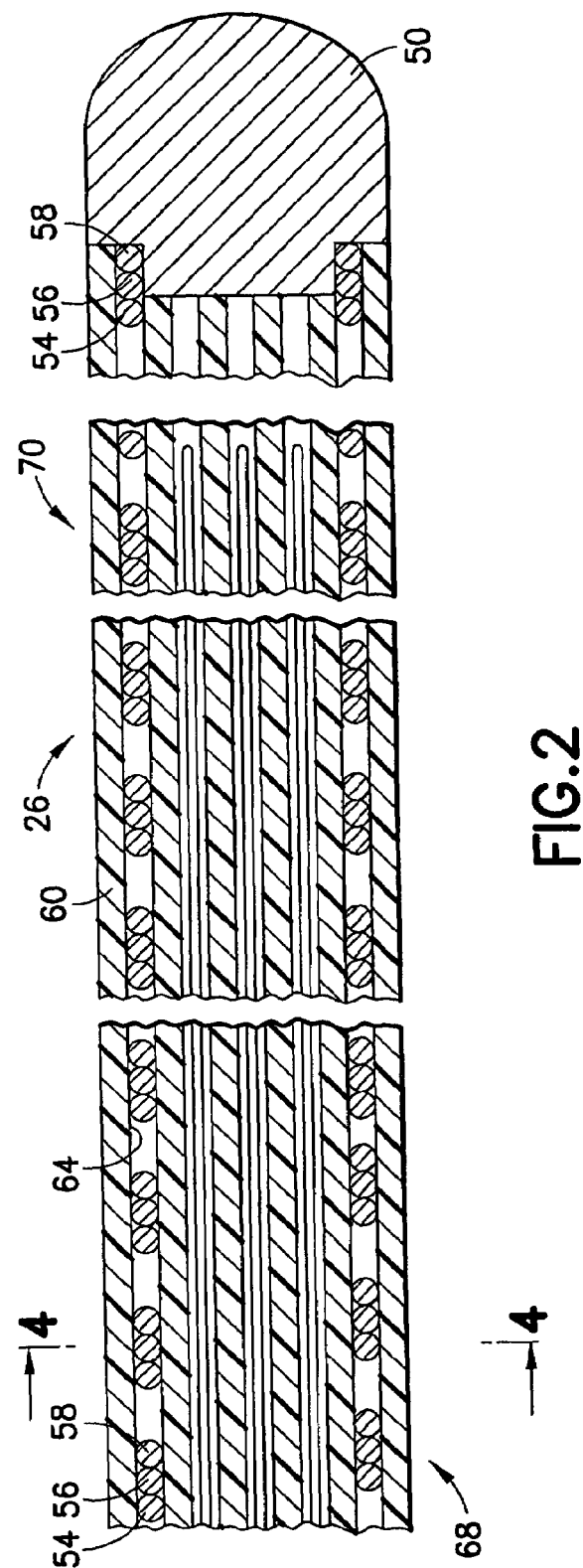
FIG. 2 is a longitudinal cross section view illustrating the lead body of the lead system embodying the invention.
Figure 3:
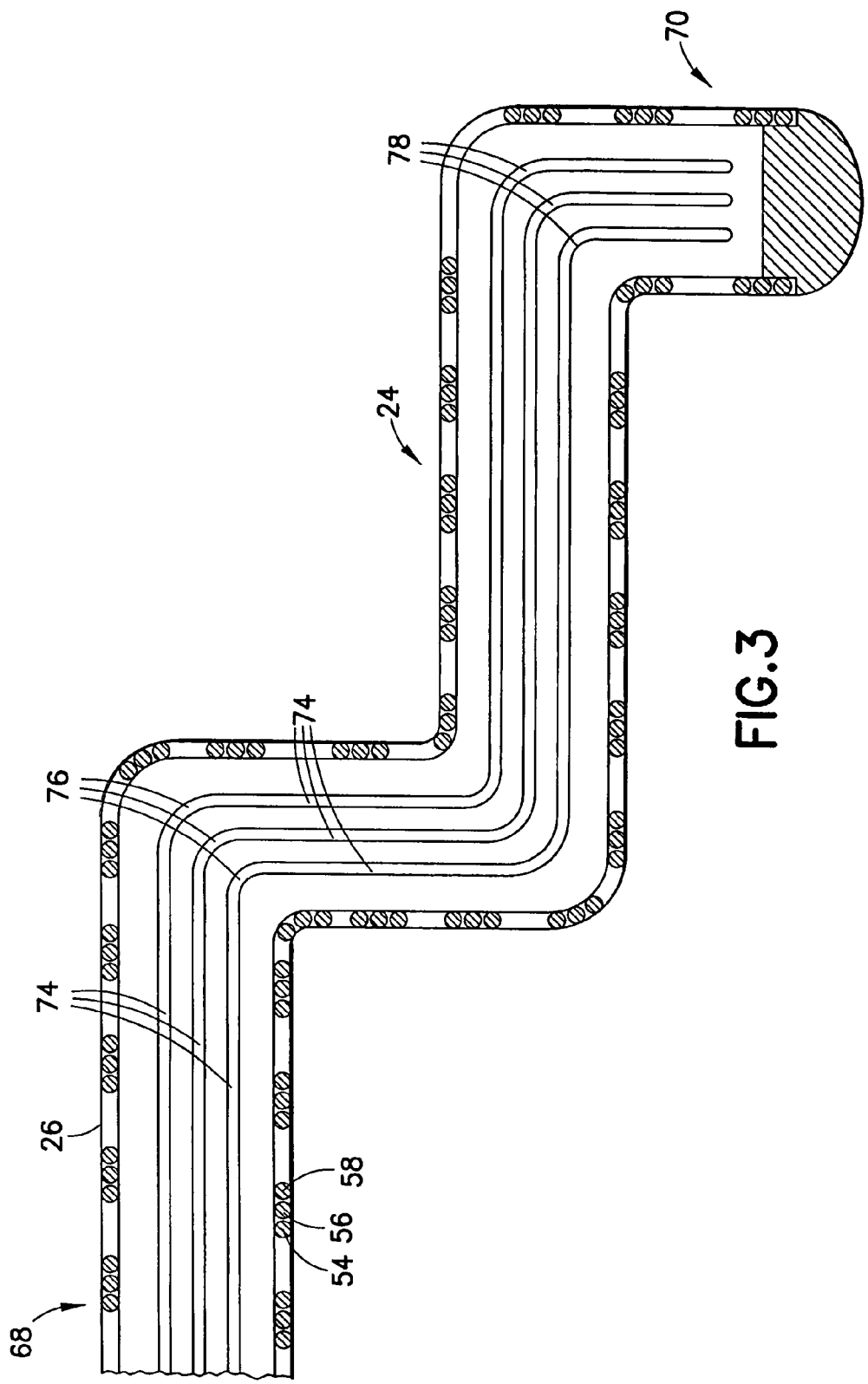
FIG. 3 is a diagrammatic longitudinal cross section view, somewhat similar to FIG. 2, but with a concentrated showing of super plastic elements within the lead body.
Figure 4:
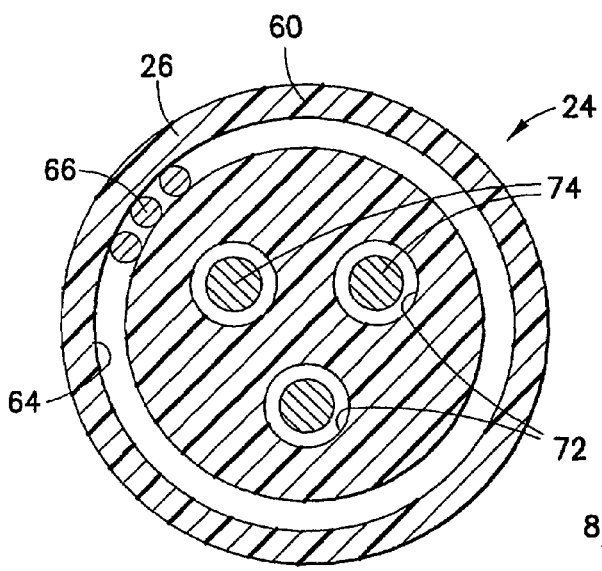
FIG. 4 is a cross section view taken generally along line 4-4 in FIG. 2.

Turning now to FIGS. 2, 3, and 4, the lead body or lead assembly 26 includes an elongated insulative sheath 60 of flexible resilient material having at least one longitudinally extending lumen 64. In these figures, electrical conductors 55, 56, 58 of coil configuration are received within the lumen 64 of the insulative sheath and extend between a proximal end 68 and a distal end 70 of the lead body. While three conductors are illustrated, the invention need not be so limited. Any appropriate number of conductors would satisfy the purposes of the invention.

With the construction illustrated in FIGS. 2-4 at least one additional lumen 72 is provided, actually three being illustrated for purposes of explanation. Into each lumen 72, at least one elongated super plastic element 74 is slidably received, the super plastic element being bendable, as at 76 and 78 in FIG. 3, to configure the lead assembly 24 to negotiate tortuous turns in the vasculature of the body as seen in FIG. 1. If one super plastic element 74 is of sufficient strength to maintain a desired bend, that is all that would be necessary for the construction of a lead assembly. However, it might be necessary to use two or more super plastic elements 74 in the manner shown in FIGS. 2-4 to maintain a desired bent configuration of the nature illustrated in FIG. 3.

This new metal, super plastic alloy 72, is described in the Apr. 18, 2003 edition of Science Magazine, Vol. 300 at page 464 as:

" . . . a group of alloys that exhibit 'super' properties, such as ultralow elastic modulus, ultrahigh strength, super elasticity, and super plasticity, at room temperatures and that show Elinvar and Invar behavior. These "super" properties are attributable to a dislocation-free plastic deformation mechanism. In cold-worked alloys, this mechanism forms elastic strain fields of hierarchical structure that range in size from the nanometer scale to several tens of micrometers. The resultant elastic strain energy leads to a number of enhanced material properties."

As seen in FIG. 1, the terminals 42, 44, 46 comprise an electrical connector 80 coupled to the proximal end of the conductors 54, 56, 58 for releasable attachment to the stimulating pulse generator or device 20. Also, as seen in FIGS. 2 and 3, the distal ends of the conductors 54, 56, and 58 are coupled to the distal end of the electrode 50.

Figure 5:
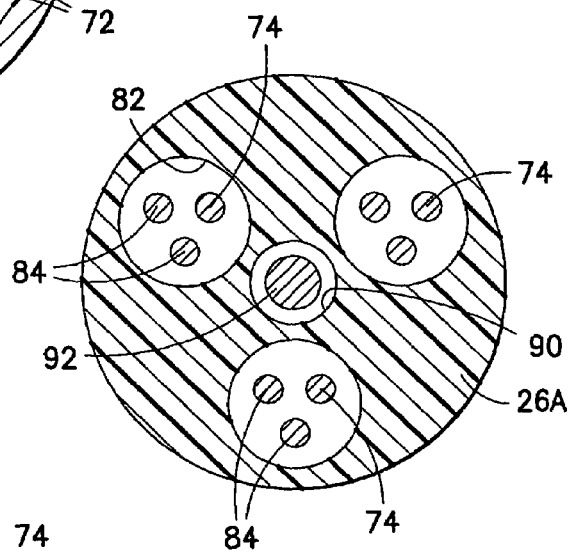
FIG. 5 is a cross section view of another embodiment of the invention.

In another embodiment, as seen in FIG. 5, a lead body 26A of flexible resilient material has a plurality of lumina 82 similar to the lumina 72 and a super plastic element 74 received in each lumen. This design may also include one or more cable conductors 84 in each lumen 82 such that the conductors and super plastic elements each share the same lumen.

Figure 6:
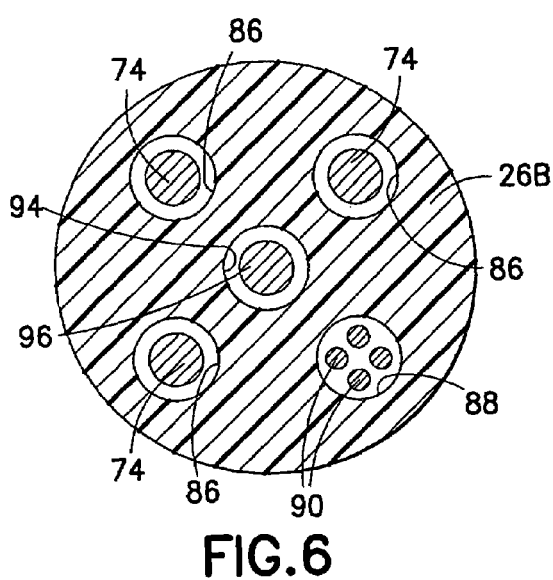
FIG. 6 is a cross section view of still another embodiment of the invention.

In still another embodiment, as seen in FIG. 6, a lead body 26B of flexible resilient material has a plurality of lumina 86 similar to the lumina 72 and 82 and a super plastic element 74 received in each lumen 86. For this design, yet another lumen 88 may contain a plurality of cable conductors 90.

In the FIG. 5 embodiment, the lead body 26A may include yet another lumen 90 extending longitudinally between its proximal and distal ends for selective reception of a stylet 92 to aid in implanting that lead system. Similarly, in the FIG. 6 embodiment, the lead body 26B may include yet another lumen 94 extending longitudinally between its proximal and distal ends for selective reception of a stylet 96 to aid in implanting that lead system.

To use the foregoing construction of the lead assembly 24 to best effect, one or more super plastic elements 74 are slidably inserted into the appropriate lumina of the insulative sheath 60, then, using the stylet, bent at the locations 76 and 78 of FIG. 3 to configure the lead assembly so that it is able to negotiate the tortuous turns in the vasculature of the body as illustrated in FIG. 1. Each super plastic element is cold worked until it achieves the appropriate ductility to be able to negotiate the afore-mentioned tortuous turns. Such cold working may be accomplished before implantation of the lead assembly in the body, or it may be accomplished after implantation.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An implantable lead assembly for a body implantable medical system adapted to transmit electrical signals between a proximal end portion of the lead assembly and a distal end portion of the lead assembly to thereby stimulate selected body tissue comprising:
    an elongated insulative sheath of flexible resilient material having at least one longitudinally extending lumen;
    an electrical conductor received within the lumen of the insulative sheath and extending between a proximal end and a distal end;
    at least one elongated super plastic alloy element slidably received within the lumen of the insulative sheath, the super plastic alloy element being bendable to configure the lead assembly to negotiate tortuous turns in the vasculature of the body;
    an electrical connector coupled to the proximal end of the conductor for releasable attachment to a stimulating pulse generator; and
    an electrode coupled to the distal end of the conductor;
    wherein the super plastic alloy element has a dislocation-free plastic deformation mechanism.

2. An implantable lead assembly as set forth in claim 1 wherein the electrical conductor and the super plastic alloy element share the same lumen.

3. An implantable lead assembly as set forth in claim 1 wherein the insulative sheath has a plurality of lumina and a super plastic alloy element received in each lumen.

4. An implantable lead assembly as set forth in claim 1 wherein the insulative sheath has a plurality of lumina; and wherein a super plastic alloy element and a conductor is received in each lumen.

5. An implantable lead assembly as set forth in claim 1 wherein a plurality of super plastic alloy elements and a conductor are received in each lumen.

6. An implantable lead assembly as set forth in claim 1 wherein the insulative sheath has a lumen extending longitudinally between a proximal end at the proximal connector and a distal end at the distal tip electrode for selective reception of a stylet for aid in implanting the lead system.

7. An implantable lead assembly as set forth in claim 1 wherein the super plastic alloy element comprises a super plastic alloy.

8. An implantable lead assembly as set forth in claim 1 wherein the super plastic alloy element comprises a super plastic titanium.

9. A method of implanting a lead assembly including an electrical conductor extending between a proximal end and a distal end and an insulative sheath covering the conductor and having an elongated lumen extending therethrough, the lead assembly provided for a body implantable medical system adapted to transmit electrical signals between a proximal end portion of the lead assembly and a distal end portion of the lead assembly to thereby stimulate selected body tissue comprising:
    (a) slidably inserting into the lumen of the insulative sheath an elongated super plastic alloy element, the super plastic alloy element having a dislocation-free plastic deformation mechanism; and
    (b) bending the super plastic element to configure the lead assembly to negotiate tortuous turns in the vasculature of the body.

10. A method as set forth in claim 9 and further comprising:
    (c) coupling an electrical connector to the proximal end of the conductor for releasable attachment to a stimulating pulse generator; and
    (d) coupling an electrode to the distal end of the conductor.

11. A method as set forth in claim 9 and further comprising:
    (c) slidably inserting into the lumen of the insulative sheath both the super plastic alloy element and the electrical conductor.

12. A method as set forth in claim 9 and further comprising:
    (c) providing a plurality of lumina in the insulative sheath; and
    (d) slidably inserting a super plastic alloy element into each lumen of the insulative sheath.

13. A method as set forth in claim 9 and further comprising:
    (c) providing a plurality of lumina in the insulative sheath; and
    (d) slidably inserting into each lumen of the insulative sheath both a super plastic alloy element and an electrical conductor.

14. A method as set forth in claim 9 and further comprising:
    (c) providing a plurality of lumina in the insulative sheath; and
    (d) slidably inserting a super plastic alloy element into each lumen of the insulative sheath.

15. A method as set forth in claim 9 and further comprising:
    (c) providing at least one lumen in the insulative sheath; and
    (d) slidably inserting into the lumen of the insulative sheath a conductor and a plurality of super plastic alloy element.

16. A method as set forth in claim 9 and further comprising:
    (c) providing in the insulative sheath a specified lumen for reception of a stylet; and
    (d) inserting into the specified lumen a stylet for aid in implanting the lead system.

17. A method as set forth in claim 9 and further comprising:
    (c) cold working the super plastic element until it achieves the appropriate ductility to be able to negotiate the tortuous turns in the vasculature of the body.

18. The method as set forth in claim 17 and further comprising:

(d) cold working the super plastic alloy element before implantation of the lead assembly in the body.

19. The method as set forth in claim 17 and further comprising:

(d) cold working the super plastic alloy element after the lead assembly is implanted in the body.

* * * * *